United States Patent [19]

Chadha et al.

[11] Patent Number: 4,485,038

[45] Date of Patent: Nov. 27, 1984

[54] METHOD FOR THE PRODUCTION AND PURIFICATION OF HUMAN LEUKOCYTE INTERFERON

[75] Inventors: Kailash C. Chadha, West Seneca; Eugene Sulkowski, Buffalo, both of N.Y.

[73] Assignee: Health Research (Roswell Park Division), Buffalo, N.Y.

[21] Appl. No.: 435,295

[22] Filed: Oct. 19, 1982

[51] Int. Cl.$^3$ .................... C07C 103/52; A61K 45/02; C12P 21/00; C07G 7/00

[52] U.S. Cl. ................................. 260/112 K; 424/85; 435/68; 435/811

[58] Field of Search ...................... 424/85; 260/112 R; 435/68, 811

[56] References Cited

U.S. PATENT DOCUMENTS

| | | | |
|---|---|---|---|
| 4,168,261 | 9/1979 | Edy | 424/85 |
| 4,257,938 | 3/1981 | Hosoi et al. | 424/85 |
| 4,266,024 | 5/1981 | Swetly et al. | 424/85 |
| 4,289,689 | 9/1981 | Friesen et al. | 424/85 |
| 4,296,025 | 10/1981 | Sugimoto | 424/85 |
| 4,311,639 | 1/1982 | Ganfield et al. | 424/85 |

OTHER PUBLICATIONS

Cantell et al., Large-scale Production of Human Leukocyte Interferon Containing 10° Units per ml; *J. Gen. Virol.* 39: 541-543, (1978).

Zoon et al., Purification and Partial Characterization of Human Lymphoblastoid Interferon; Proc. Natl. Acad. Sci., USA 76(11): 5601-5605, (1979).

White et al., Large-scale Production of Human Lymphoblastoid Interferon, Cancer Treatment Reviews 7: 245-252, (1980).

Yonehara et al., Purification of Human Lymphoblastoid Interferon by a Simple Procedure with High Yields, The Journal of Biological Chemistry, vol. 256, No. 8, Apr. 25, pp. 3770-3775, (1981).

Staehelin et al., Purification and Characterization of Recombinant Human Leukocyte Interferon (IFLrA) with Monoclonal Antibodies, The Journal of Biological Chemistry, vol. 256, No. 18, Sep. 25, pp. 9750-9754, (1981).

Marc de Ley et al., Interferon Induced in Human Leukocytes by Mitogens: Production, Partial Purification and Characterization, Eur. J. Immunol., (1980), 10:877-833.

Rubinstein et al., Human Leukocyte Interferon: Production, Purification to Homogeneity, and Initial Characterization, Proc. Natl. Acad. Sci. USA, vol. 76, No. 2, pp. 640-644, Feb. 1979.

van Oss et al., Two Methods for the Removal of Erythrocytes from Buffy Coats for the Production of Human Leukocyte Interferon–Immunological Communications, 10(6), 549-555, (1981).

Erickson, J. S. and Paucker, K.; Purification of Acid Ethanol-Extracted Human Lymphoid Interferons by Blue Sepharose Chromatography–Analytical Biochemistry 98, 214-218, (1979).

Yonehara et al., Purification of Human Lymphoblastoid Interferon by a Simple Procedure with High Yields; Journal of Biological Chemistry, 256 (8), 3770-3775, (1981).

Chada, K. C. and Sulkowski, E., Chromatography of Human Leukocyte Interferon on Controlled-pore Glass, Prep. Biochem. 11, 467-482, (1981), published 10/20/1981.

Chada, K. C. and Sulkowski, E., Adsorption of Human Alpha (Leukocyte) Interferon on Glass: Contributions of Electrostatic and Hydrophobic Forces, (1982).

Cantell, K. et al., Partial Purification of Human Leukocyte Interferon on a Large Scale, Methods in Enz. 78, 499-505, (1981).

Yjimoto et al., Chemical Abstracts: 95:13364h, (1981).

Jost et al., Chemical Abstracts: 96:118346C, (1982).

Miyajima et al., Chemical Abstracts: 96:192275v, (1982).

Berg, K. and Heron, I., The Complete Purification of Human Leucocyte Interferon, Scand. J. Immunol. 11, 489-502, (1980).

*Primary Examiner*—Blondel Hazel
*Attorney, Agent, or Firm*—Christel, Bean & Linihan

[57] ABSTRACT

A process for the production and purification of human interferon derived from leukocyte of lymphoblastoid cell origin characterized by a sequence of steps involving chromatography of a solution of crude interferon on porous glass, utilizing three new classes of eluants for recovering the interferon bound to the porous glass, followed by cation exchange chromatography and finally chromatography on a hydrophobic sorbent material which process produces a final purified interferon in its natural form containing those protein components which are normally labile to low pH treatment along with those components which are pH stable. In one aspect, the improved method of purification also includes the optional molecular filtration of the crude interferon prior to initiating the purification process. In yet another embodiment, a new process for producing crude interferon from buffy coat cells utilizing a starch-gel agglomeration and sedimentation technique is also described.

15 Claims, No Drawings

METHOD FOR THE PRODUCTION AND PURIFICATION OF HUMAN LEUKOCYTE INTERFERON

The invention described herein was made, in part, in the course of work under grant No. NOI-HB-2920 awarded by the National Heart, Lung And Blood Institute. The government has certain rights in this invention.

BACKGROUND OF THE INVENTION

1. Field of the Invention

The present invention relates to a method for the production and purification of leukocyte interferon. More particularly, the present invention is directed to an improved method for producing and purifying human interferon derived from human leukocyte or lymphoblastoid cell origin.

2. Description of the Prior Art

Interferons are proteinaceous substances which are capable of making living cells resistant to infection caused by viral and nonviral agents. Interferons are also known to act as potent immuno-regulators and as antineoplastic agents.

Interferon activity derived from leukocytes is due to the presence of at least 9-11 different protein components. Therefore, it is important that the isolation of interferon from biological fluids should preserve all existing components. Moreover, the purification procedure used to isolate interferon in its natural multi-component state should be carried out under mild enough conditions to prevent any structural or conformational modifications of the underlying individual proteins. In order for the full prophylactic and therapeutic potential of interferons to be realized, it is essential that the conditions described above be fully met.

Several procedures have been developed for the purification of human interferon derived from leukocytes and lymphoblastoid cells (Namalva). These know procedures usually involve several complex steps and are not ideally suited for efficient large scale, commmercial production. Also, the recovery of interferon produced by these procedures varies considerably. The final interferon yield may be anywhere between 10% to 70% of the starting material.

The majority of human interferon used today is produced and purified essentially according to the procedure developed by Kari Cantell et al. as described in "Partial Purification Of Human Leukocyte Interferon On A Large Scale" appearing in *Methods In Enzymology*, Volume 78, pages 499-505 (and the other articles cited therein). These methodologies involve the use of ammonium chloride to lyse red blood cells, low pH treatment of the crude interferon preparation for the purpose of inactivating the inducer virus and the use of harsh chemicals such as ethanol or potassium thiocyanate. Others have purified leukocyte interferon by using various sorbents including glass or a specific antibody immobilized to a solid support. In either case, interferon desorption was accomplished by using harsh chemicals like ethanol, potassium thiocyanate or low ph (highly acidic) buffers. However, the human interferon purified by these procedures may not be in its natural form. The use of the ammonium chloride to lyse red blood cells has been shown to be responsible for the loss of about 30% to 40% of leukocytes. Ammonium chloride treatment also damages granulocytic membranes causing the release of proteases capable of inactivating interferon. The low pH treatment results in the loss of the "pH2-labile" leukocyte interferon component which is believed to have a significantly higher level of antitumor activity than the "pH-stable" interferon component. The use of harsh chemicals such as potassium thiocyanate which is a chaotropic salt, is known to disrupt the tertiary structure of proteins, thereby causing a significant loss of antiviral activity and a considerable variation in the amounts of interferon recovered from one batch to another.

In addition, conventional interferon purification technology usually involves several steps requiring numerous intervening concentration and dialysis operations. Such procedures greatly increase the time required for interferon purification and often lead to substantial product loss due to the frequency of mechanical handling required.

The present invention achieves results never before attained in the art, namely efficient, economical commercial production of human leukocyte interferon in its natural form. Both the preparation of cells and the composition of interferon induction media are substantially new. The purification procedure, according to the present invention, is milder than any other such procedures known to date. Finally, the new process, as described herein, successfully avoids all of the drawbacks associated with the Cantell and other methodologies recited above. In particular, this process specifically results in the preservation of the "ph2-labile" interferon component which, until now, has been destroyed by all other state of the art procedures.

SUMMARY OF THE INVENTION

Accordingly, it is a primary object of the present invention to provide an improved method for the large scale production of human leukocyte interferon which is simple, milder (in terms of isolation conditions employed), more efficient and cost effective.

It is a further object of the present invention to provide a method for producing human interferon which will yield consistently higher recoveries of interferon in its natural form having a higher specific activity than those products obtainable using the existing production processes.

It is a further object of the present invention to provide a method for purifying human interferon wherein all of the process steps can be carried out "in tandem", thus minimizing the time required for carrying out the process and reducing product loss attributed to the number of individual operations presently required by known production processes, such as mechanical handling, dialysis, concentration, etc.

It is a further object of the present invention to provide an improved method for the production of human interferon which will result in an interferon recovery of between about 75%-90%.

It is a further object of the present invention to provide an improved method for producing human interferon wherein the reproducability of the results obtained will not vary substantially from batch to batch.

The present invention provides an improved method for producing and purifying interferons induced in human leukocytes or lymphoblastoid cells by a viral inducer. For the purpose of simplification, the "production" of interferon will be considered a separate procedure as compared with the "purification" of interferon even though the purification process is an essential part of the overall production of interferon which is suitable for clinical use. The production phase generally includes three principal elements: (i) the isolation of leukocytes, (ii) the maintenance of suitable conditions in the interferon production medium, and (iii) the selection of a viral inducer and its compulsory inactivation.

In one aspect thereof, the improved method for producing human interferon, according to the present invention, is characterized by the steps of (a) utilizing a "starch-gel agglomeration and sedimentation" technique for the initial isolation of leukocytes from buffy coat cells, (b) the addition of a known protein supplement such as a-gamma serum or a-gamma plasma (human) to the production medium which supplement has been pretreated (prepurified) to eliminate those proteins which would tend to bind or copurify with the interferon and which are not required for interferon production, and (c) the utilization of a virus (Sendai) preparation which has also been pretreated (prepurified) to eliminate those proteins recited in (b) above.

In yet another aspect, the improved method for purifying human interferon, according to the present invention, is characterized by the steps of (d) optional molecular filtration of the interferon prepared at the end of the induction period (designated as crude interferon) to remove the inducer virus and other high molecular weight proteins, (e) adsorption chromatography of the crude human leukocyte derived interferon on a porous glass adsorption medium such as controlled-pore glass (CPG) or silicic acid and transferring the glass (sediment) onto a column, (f) displacing the interferon retained on the porous glass medium with any of the following eluants either separately or in combination tetraalkylammonium chlorides such as tetramethylammonium chloride and tetraethylammonium chloride at concentrations ranging from 0.1 to 1.0 M; alkylamines such as methylamine, dimethylamine, trimethylamine or tetramethylamine at concentrations ranging from 0.1 to 0.5 M; or cosolvent eluant mixtures comprising electrolytes such as sodium chloride or ammonium chloride preferably buffered with Tris.HCl in combination with polarity reducing agents such as ethylene glycol and/or propylene glycol, (g) charging the eluant to a cation exchanger such as CM-Sepharose CL-6B or any other carboxymethyl type of ion exchanger at a pH above about 4.0 (moderately acidic conditions) causing the interferon to be retained, and subsequently recovered by raising the pH and the ionic strength of the eluant, (h) thereafter charging the eluate obtained from the cation exchanger column to a hydrophobic sorbent material such as phenyl-agarose and (i) optionally, subjecting the eluate obtained from the phenyl-agarose column to molecular seiving on any commercially available seiving medium having about a 50,000 molecular weight cut off (an AcA$_{54}$ column is preferred for this purpose).

It should be noted that the above process may be carried out sequentially or in tandem, (i.e., as a continuous process without interruption between the individual steps) thereby greatly reducing the time required for purification.

The overall specific activity of the final product obtained, according to the instant invention, is approximately $1 \times 10^7$ units per mg of protein as a result of about a 1000-fold purification.

The foregoing and additional advantages and characterizing features of the present invention will become clearly apparent upon a reading of the ensuing detailed description together with the included examples.

DETAILED DESCRIPTION OF THE INVENTION

The human leukocyte cells suitable for use in producing the crude interferon which is to undergo purification according to the instant invention may be obtained from buffy coats, by centrifugation of peripheral blood available from blood banks, ascites and bone marrow aspirate, etc. In addition, leukocytes obtained from cultured established human leukocytes (Namalva or DG-75 cells) or leukocytes obtained by any other conventional method can also be used in the present purification scheme.

Production Of Crude Interferon From Buffy Coat Cells

Leukocytes obtained from buffy coats may be produced according to the following newly proposed procedure. The leukocytes are separated from contaminating red blood cells by mixing the buffy coat cells with a starch solution (PG-260; manufactured by Penick & Ford) or hydroxyethyl starch (Volex; manufactured by McGaw Laboratories) solution and allowing the cells to settle by gravity sedimentation. The top layer containing the leukocytes is collected, the cells washed with physiologicalsaline, and cell pellet resuspended in interferon induction media to give a final cell concentration of between $2 \times 10^6$ to $1 \times 10^7$ cells per ml. Interferon induction media can be minimal essential medium, RPMI 1640, 199 medium or any other synthetic or semisynthetic media designed for the growth of suspension cells.

Any known Type I interferon inducer (viral or nonviral) can be employed to induce Type I interferon from human leukocyte cells regardless of the source of such cells. Sendai virus, Necastle disease virus, blue tongue virus or double stranded RNA can be used as interferon inducers. The concentration of each inducer can vary over a wide range. The priming of cells with low dosages of interferon (20 to 300 units) for about 30 to 120 minutes prior to interferon induction can also be used with beneficial effects on interferon induction.

A certain level of protein supplement is usually required during the interferon induction phase for maximal interferon production. Such supplements may include human serum or human a-gamma serum or human a-gamma plasma at concentrations varying anywhere between 2% to 10% (v/v) of the interferon production medium, or other known protein supplements. Interferon induction is usually carried out for 20 hours at 37° C. in a 5% $CO_2$ atmosphere. In case it is not feasible to gas the medium, tricine (3 g/l) and sodium bicarbonate (2.4 g/l) may be added to the interferon production medium in order to maintain the proper pH through out the production phase.

The inducer virus and the protein supplement used during the interferon production phase may be further processed to remove certain proteins which are not essential for maximal interferon yield.

For example, human a-gamma plasma is preferably chromatographed sequentially on both porous glass beads and phenylagarose under the same chromatographic conditions (i.e. pH, eluants, etc) that are used for interferon purification. When human a-gamma plasma is first chromatographed on CPG, nearly 85% of the protein appears in the breakthrough fraction. This latter fraction is then chromatographed on Phenyl- Sepharose CL-4B and again the majority of proteins (80%) appear in the breakthrough region. The serum proteins that appear in the breakthrough region of the phenyl-agarose column are used for interferon production.

The Sendai virus is also preferably chromatographed on phenyl-agarose where 90% of the virus appears in the breakthrough region. This breakthrough virus is used for interferon production.

This approach of prepurifying the reagents used in interferon production to eliminate those nonessential proteins that would otherwise bind or copurify with the interferon when it is chromatographed on glass or silica adsorbents, is believed to be a totally new concept never before recognized in the prior art.

Purification Of Crude Interferon

The purification procedure according to the present invention eliminates those treatment conditions which may be deleterious to the various protein components present in leukocyte derived interferon. The viral inducer is not inactivated by lowering the pH of the interferon preparation to 2.0 for 2 to 5 days. Such a treatment, if carried out, results in the loss of the "pH2-labile" interferon component which may comprise anywhere from 30% to 60% of the total interferon and whose physiologica significance is not yet known. The new process uses an alternate means of removing the inducer virus. A series of affinity chromatography steps have been developed which effectively remove all detectable traces of the infectious virus. The majority of Sendai virus can also be removed if the interferon preparation is subjected to membrane sieving or to molecular filtration with a 100,000 MW cut off filter.

The crude interferon preparation obtained at the end of the production phase is preferably first filtered through a 100,000 MW cut off filter to remove the inducer virus and other high molecular weight proteins and then concentrated 10 fold utilizing another filter with 10,000 MW cut off to reduce the volume of the starting material prior to the affinity chromatography steps. The filters are primed with human serum albumin to minimize the losses of interferon activity. Filtration is usually carried out at 4° C. Molecular filtration usually results in 5 to 10 fold purification of interferons.

The porous glass exchange medium to be used as the adsorbent in the first step of the chromatographic purification procedure according to the present invention is commercially available under several Trade Marks and may be manufactured in bead form having a "controlled pore size". For instance, controlled-pore glass (CPG) or silicic acid may be used in the instant process. Depending upon the volume of interferon to be processed, the CPG or silicic acid can be either packed in a column or used in a simple batch type operation. In either case, the sorbent is first equilibrated with a phosphate buffer at or near the neutral pH. Crude interferon, either filtered or not filtered, is applied to the column where all the interferon and some of the cellular proteins are retained. The column is then washed with more of the equilibrating buffer and subsequently equilibrated with the buffer to a pH of about 8.0.

It has now been discovered that human leukocyte interferon can be efficiently recovered in its natural form from controlled pore glass or silicic acid by the use of certain specified eluants at low concentrations which eluants result in the stabilization of the interferon molecule. According to the present invention, bound interferon may be displaced from the glass columns with any of the following eluants either separately or in combination: (1) tetraalkylammonium salts such as tetramethylammonium chloride or tetraethylammonium chloride at concentration ranges of 0.1 to 1.0 M; (2) alkylamines such as methylamine, dimethylamine, trimethylamine or tetramethylamine at concentration ranges of 0.1 M-0.5 M; 3) by a mixture of suitable cosolvents which individually are either polar or apolar, as for example, the combination of ethylene glycol or propylene glycol with a suitable electrolyte such as NaCl or $NH_4Cl$, although at considerably higher molar concentrations than that of an alkylamine. It is preferable to buffer the cosolvent mixture with Tris.HCl, pH 8.0 for optimum recovery.

The chromatography of proteins on controlled-pore glass (CPG) is known and has been extended to the purification of interferons. However, this procedure remains a relatively new technique which is largely empirical. Proteins bound to CPG have been eluted by a variety of means: change in ionic strength, pH and by the use of chaotropic salts. Interferons have been displaced from glass with ethylene glycol, potassium thiocyanate and at pH2. The procedure, according to the instant invention, now introduces 3 new classes of eluants which do not result in a gross perturbation of the conformation of the interferon molecule.

The eluting power of tetraalkylammonium salts has been attributed to their dual character as hydrophobic electrolytes since the molecules have both apolar and polar properties. Similarly, it has now been discovered that the eluting efficacy of tetraalkylammonium salts can be mimicked by a mixture of suitable cosolvents which individually are either polar or apolar. In addition, it has been found that the more hydrophobic an alkylamine, the more efficacious it is as an eluant of interferon from a glass surface.

Clearly, tetramethyl- and tetraethylammonium chlorides are the most efficient eluants. Other tetraalkylammonium salts may also be useful in the instant procedure as long as the leukocyte interferon remains stable when exposed to such salts. Since it has been determined that an elongation of the alkyl arm of the ammonium cation causes a significant drop in interferon activity, it is the tetramethyl- and tetraethylammonium chlorides which may be useful as eluants at a 1 molar concentration (or less).

Similarly, it has now been found that specific alkylamines may be used to safely and efficiently elute leukocyte interferon. The elution efficacy of an alkylamine is a function of the extent of its alkylation. Full recovery of interferon can be accomplished with tetramethylamine at 0.2 M concentration whereas the concentration of trimethylamine must be 0.3 M to be equally effective. Similarly, methylamine is less effective than dimethylamine and, in turn, dimethylamine is less effective than trimethylamine. A little difference in eluting power between trimethylamine and tetramethylamine is expected since column chromatography performed at a convenient speed is most likely done within a time interval much smaller than required for the attainment of equilibrium. This effect will tend to minimize the differential in eluting efficacy of the higher homologs of the alkylamine series.

In the past, the use of ethylene glycol as the sole eluant resulted in only about a 40% recovery of human interferon from CPG. Furthermore, electrolytes such as NaCl used alone failed to elute the interferon. By contrast, according to the present invention, it is possible to accomplish nearly complete recovery of interferon with 25% ethylene glycol (4.2 M) provided it is combined with NaCl (1 M) as a cosolvent. Thus, it has now been discovered that it is necessary to use both ethylene glycol and sodium chloride as cosolvents in order to achieve the efficient desorption of interferon from glass. Apparently, an efficacious eluant must counteract both hydrophobic and electrostatic interactions. Similar results may be obtained using ethylene glycol or propylene glycol combined with $NH_4Cl$ as a cosolvent.

In addition, it has been found that the eluting power of such cosolvent mixtures may be affected by the presence of a buffer. The combination of ethylene glycol with NaCl containing 0.1 M Tris.HCl (pH 8.0) produced an almost complete recovery of interferon activity using only 12.5% ethylene glycol (2.1 M) while, the presence of a suitable phosphate buffer required the presence of 25% ethylene glycol (4.2 M) to achieve the same result. Apparently, $Tris^+$ cation has a higher affinity for the glass surface than the $potassium^+$. This affinity may be due, in part, to its hydroxymethyl groups.

Finally, it has been shown that the substitution of $NH_4Cl$ for NaCl in the eluant cosolvent containing ethylene glycol produces the same eluting efficacy.

Interferon recovery during the initial elution from CPG or silicic acid utilizing the new eluants specified above, is usually between 85% to 100%. This step also results in about a 10 to 40 fold purification of interferons. A higher purification factor is usually achieved if the starting interferon preparation is first processed through the optional molecular filtration step.

The next essential step of the present purification procedure utilizes cation exchange chromatography. The pH of the interferon solution obtained from the CPG or silicic acid column is adjusted to between 4.0 to 5.0 and the interferon is then applied to a column filled with a suitable cation exchanger such as CM-Sepharose CL-6B equilibrated with a sodium acetate buffer having a pH of 4.5. At this pH, nearly all the interferon (about 95%) is retained on the ligand. The bound interferon is then displaced when the column is eluted with a pH 7.0-8.0 buffer containing sodium chloride varying in concentration from 0.15 M to 1.5 M. Interferon recovery during this step is usually 85% to 90% and results in about a 3 to 10 fold purification. This step also effectively eliminates any tetraalkylammonium salt which, if present, would otherwise interfere with the next separation process involving hydrophobic chromatography.

Depending upon the volume of interferon to be processed, this cation exchange step can be carried out either in a column or as a batch operation.

It should be noted that the chromatography of the interferon on the cation exchanger is performed at a pH not lower than 4.5 and not higher than 9.0. This pH range is known to be safe for the majority of protein components. As a result of this higher pH treatment, the "pH labile" component of the interferon is preserved throughout this step without any significant loss of interferon activity. As an additional security measure, the adsorption of the interferon on the cation exchanger can be carried out in a batchwise manner to minimize the time of interferon exposure (about 60 to 90 minutes) to a pH of 5.0.

The next step of the instant process utilizes hydrophobic chromatography. The conditions of displacing interferon from the cation exchanger as recited above (phosphate buffer, pH7.4, containing 0.5 M NaCl) are compatable to the binding of the interferon to a hydrophobic sorbent such as phenyl-agarose. Phenyl-agarose can be obtained from a variety of commercial sources. Phenyl-Sepharose CL-4B is available from Pharmacia Fine Chemicals, Piscataway N.J. The interferon from the cation exchange step is applied directly to the Phenyl-Sepharose CL-4B column equilibrated with a phosphate buffer having a pH of 7.4 and containing 0.5 M NaCl. Interferon retention is usually about 100%. The bound interferon is displaced when the salt is removed from the eluting buffer and replaced with about 50% to 70% ethylene glycol. This step results in an interferon recovery between about 80% to 95% with an approximate 10 to 15 fold purification.

The elution of interferon from the hydrophobic sorbent is performed with ethylene glycol which is known to be safe for this type of interferon. The use of ethylene glycol as an eluant can also be totally eliminated provided that the ligand has a density which is lower than 40 $\mu$moles per ml of phenylagarose. Bethesda Research Laboratory manufactures a phenylagarose that is approximately 27 $\mu$moles per ml of phenyl and which can be used for this purpose.

The interferon recovered from the phenyl-agarose can be dialyzed to remove all traces of ethylene glycol, filtered, sterilized and lyophilized. The interferon purified by the procedure, according to the instant invention, and lyophilized has been subjected to all FDA required safety testing and has been shown to be sterile, safe and free from pyrogens. An average specific activity of interferon purified, according to this method, is in the range of $1 \times 10^6$ to $1 \times 10^7$ ref. units/mg of protein depending upon the titer of the starting crude interferon. An additional 5 to 10 fold purification can be achieved if the interferon is further subjected to molecular sieving. Sephadex beads or other molecular filtration media can be used for this purpose.

The instant process may be effected either sequentially or "in tandem", thereby avoiding the need for any separate dialysis or concentration operations which would interrupt the continuity of the purification procedure. The choice of sequence would depend upon the quality of the final product needed. Moreover, the production and purification procedures described above are suitable for industrial scale production.

The following Examples are included for illustrative purposes only and are not intended to limit the scope of the invention.

PRODUCTION OF CRUDE INTERFERON

Example I

Leukocytes were isolated by starch gel agglomeration and sedimentation technique. Buffy coat cells were mixed in a ratio of 1:1 (v/v) with a solution of PG -260 starch [6% (w/v) solution in 0.9% sodium chloride] or Volex (6%) and allowed to stand at room temperature for 1 hour. The top layer containing the leukocytes was collected and centrifuged (400×g for 10 minutes) to separate out the starch. The leukocytes were then washed twice with sterile PBS to remove any remaining traces of starch and finally resuspended in 199 medium at a final cell density of $1 \times 10^7$ cells/ml and induced with 50-150 HAU/ml of Sendai virus or 5 PFU/cell of Newcastle disease virus. The interferon production medium also contained tricine (3 g/l), sodium bicarbonate (2.4 g/l), neomycin (20 mg/l) a-gamma plasma (4%, v/v). Interferon production was allowed to proceed for 20 hours at 37° C. At the end of this time interval, the leukocytes were removed by low speed centrifugation and the supernatant was designated as crude interferon. The interferon titer varied between 10,000 to 50,000 reference units as determined by biological assay and the protein content varied between 1.1 to 1.5 mg/ml.

Example II

Lymphoblastoid cells (DG-75) were grown as a suspension culture in RPMI 1640 medium supplemented with 10% fetal bovine serum. When the cell density reached to $2 \times 10^6$ cells/ml, the cells were pelleted by low speed centrifugation and resuspended in RPMI 1640 medium containing 2% human a-gamma plasma and induced with Sendai virus or Newcastle disease virus. The interferon production period was 20 hours, and during this time the cells were maintained at 37° C. in a 5% $CO_2$ atmosphere. The DG-75 cells were then pelleted by low speed centrifugation and the supernatant was designated as crude interferon. The average interferon titer was 5000 units and the protein content was between 1.0 to 2.5 mg/ml.

PURIFICATION OF CRUDE INTERFERON

In Examples III-VI, unless otherwise specificed, all steps were carried out at 4° C. Crude interferon prepared according to Examples I, II or by any other conventional method can be used as the starting material for the instant purification scheme.

Example III

A 50 ml solution of crude interferon containing 25,000 units of interferon per ml and 1.2 mg protein per ml was applied to a column (0.9 $\times$ 10 cm) of controlled pore glass (CPG-350 or CPG-75 Electro-Nucleonics, Inc.) equilibrated with 0.01 M potassium phosphate pH 7.2. The column was washed with 50 ml of 0.01 M potassium phosphate, pH 7.2, and then equilibrated with a 0.1 M Tris.HCl, pH 8.0. The column was then eluted with 30 ml of 0.1 M Tris.HCl, pH 8.0 buffer containing 0.3 M tetramethylammonium chloride. This latter eluate contained a total of $1.18 \times 10^6$ ref. units of interferon activity and 4 mg of protein. This represents a 15 fold purification and an interferon recovery of about 94%. The specific activity was $2.95 \times 10^5$ ref. units/mg of protein.

The pH of the interferon solution recovered from the CPG column was adjusted to 4.5 with 1 N HCl and applied directly to a column (0.9$\times$5 cm) filled with CM-Sepharose CL-6B equilibrated with 0.05 M sodium acetate buffer, pH 4.5. The column was washed with (a) a 30 ml solution of 0.05 M sodium acetate, ph 4.5; (b) a 30 ml solution of 0.02 M sodium phosphate, pH 7.4, and finally with (c) a 30 ml solution of 0.5 M sodium chloride in 0.02 M sodium phosphate, pH 7.4. The sodium chloride eluate, (c), contained $0.85 \times 10^6$ ref. units of interferon and 0.80 mg of protein. This represents an additional 3.5 fold purification and an interferon recovery of about 80%. The specific activity was $1.06 \times 10^6$ ref. units/mg of protein.

The interferon eluted from the CM-Sepharose CL-6B column was then applied to a Phenyl-Sepharose CL-4B column (0.7$\times$5 cm) equilibrated with 0.02 M sodium phosphate, pH 7.4, containing 0.5 M sodium chloride. The column was then washed with 30 ml of an equilibrating buffer. Approximately 5% of the interferon appeared in the breakthrough and wash region. The interferon retained on the Phenyl-Sepharose column was displaced when the salt (sodium chloride) was eliminated from the phosphate buffer and replaced with 50% ethylene glycol. A total of $0.8 \times 10^6$ ref. units of interferon was recovered with 0.08 mg of protein which represents an interferon recovery of about 90% and an additional 10 fold purification. The specific activity of interferon purified after these three steps was $1 \times 10^7$ ref. units/mg protein.

Example IV

A 100 ml solution of crude preparation containing 20,000 ref. units of interferon and 1.25 mg protein per ml was applied to a silicic acid column (0.9$\times$15 cm) (manufactured by Fluka Chem, Hauupange, N.Y.) equilibrated with a 0.01 M potassium phosphate buffer having a pH of 7.2. The column was then washed with 50 ml of the column equilibration buffer. Nearly 100% of interferon was retained. The column was then equilibrated with a 0.1 M Tris.HCl, pH 8.0 buffer which eluted 2% of the interferom activity. The interferon bound to the silicic acid was recovered when the column was eluted with 50 ml of the Tri. HCl buffer pH 8.0 containing 0.2 M tetramethylammonium chloride. Of the total interferon applied to the column, $1.96 \times 10^6$ ref. units were recovered with about 12.5 mg of protein. This represents a 98% recovery of interferon and a 10 fold purification.

Silicic acid from a variety of commercial sources i.e. Fluka, Sigma, and Mallinkrodt was tested giving comparable results.

The interferon recovered from the silicic acid step was then sequentially chromatographed on CM-Sepharose CL-6B and Phenyl-Sepharose CL-4B essentially according to the details described in Example III. The interferon recovery from the CM Sepharose CL-6B column was $1.47 \times 10^6$ ref. units with about 4.16 mg of protein. This represents a 75% interferon recovery and a 3 fold additional purification. The interferon recovery from the Phenyl-Sepharose CL-4B column was $1.32 \times 10^6$ units with 0.4 mg protein. The specific activity of interferon purified by these 3 steps was about $3.2 \times 10^6$ ref. units/mg protein.

Example V

Twenty liter batches of interferon were also processed in order to explore the applicability of our procedure for large scale purification. The interferon solution used in this Example contained 30,000 ref. units of interferon and 1.5 mg protein per ml. The interferon was sequentially filtered through both 100,000 MW and 10,000 MW cut off filters.

Molecular filtration is an optional procedure which is especially useful if relatively large volumes of crude interferons are to be processed (>10 liters). It is usually carried out in 2 steps. The first step involves filtering the interferon through a 100,000 MW cut off filter (Amicon, Danvers, MA) which retains a majority of the inducer virus and other high molecular weight proteins, and allows the interferon and other proteins to go through as filtrate. The second step involves filtering the interferon through a 10,000 MW cut off filter. This step can be carried out independently of step 1, or these 2 steps can be carried out sequentially. The second step essentially functions as a concentration step resulting in about a 10 fold concentration of interferon. The protein content at the end of the 2 step filtration process is usually between about 3.5 to 7.5 mg/ml and the interferon titers are anywhere between 100,000 to 500,000 reference units/ml. Each filter is primed with 5 mg/ml of human serum albumin to minimize interferon losses.

The final recovery at the end of both filtration steps carried out in this Example was $510 \times 10^6$ ref units of interferon and 15 g of protein in a total of 2 liters. In other words, each 1 ml of concentrated interferon contained 7.5 mgs of protein and 255,000 ref. units of interferon.

The concentrated interferon was mixed with either controlled pore glass (20 g/l) or silicic acid (50 g/l). Prior to mixing both the silicic acid and the CPG were washed several times with 0.01 M potassium phosphate buffer pH 7.4, to remove slow sedimenting particles. The mixture was then stirred gently using a suspended propeller for about 60-90 minutes. During this time 90%-95% of the interferon was taken up by the beads. The interferon solution was allowed to stand for 30-45 minutes to allow the CPG or silicic acid to sediment. The supernatant contained about 5%-10% of interferon which was discarded. The sedimented CPG or silicic acid was then poured into a column. The column was washed with 150 mls of a 0.01 M potassium phosphate buffer, pH 7.4, followed by 250 mls of a Tris.HCl buffer having a pH of 8.0. The bound interferon was finally eluted in 400 mls of a Tris.HCl, buffer, pH 8.0, containing 0.3 M of tetramethylammonium chloride. The interferon recovery was $459 \times 10^6$ units (90%) in a total of 1875 mgs of protein. The pH of the interferon solution was adjusted to 4.5 with 1 N HCl and mixed in a plastic roller bottle with 35 mls of the CM-Sepharose CL-6B previously equilibrated with the 0.1 M sodium acetate, pH 4.5. This mixture was allowed to rotate gently on a roller bottle apparatus such that the beads remained in suspension. At the end of 90 minutes, the roller bottle was allowed to stand upright to allow the beads to sediment by gravity. The supernatant usually contained about 5% of interferon which was discarded. The CM-Sepharose CL-6B beads were then packed in a column and washed with the equilibration buffer. The bound interferon was recovered when the column was eluted with 200 mls of 0.02 M sodium phosphate buffer containing 0.5 M sodium chloride. A total of $395 \times 10^6$ units of interferon activity in 470 mgs of protein was recovered. This represents an 86% interferon recovery and a 4 fold additional purification.

Two hundred mls of interferon solution recoverd from the CM-Sepharose CL-6B column was applied directly to a Phenyl-Sepharose CL-4B column ($0.9 \times 10$ cm) previously equilibrated with a 0.02 M phosphate buffer, pH 7.4 containing 0.5 M sodium chloride. The column was subsequently washed with an additional 100 mls of the same buffer. The interferon retention was usually 100% and no interferon activity appeared during the wash step. The bound interferon was displaced when the column was eluted with 100 ml of 0.02 M sodium phosphate containing 50% ethylene glycol. A total of $355.5 \times 10^6$ units of interferon activity with 49 mg of protein was recoverd. This represents a 90% interferon recover during this step and about an additional 9 fold purification. The specific activity of the final product was $7.25 \times 10^6$ ref. units/mg protein.

Example VI

One hundred mls of interferon from Example II (lymphoblastoid type) containing 5000 ref. units of interferon activity and 1 mg of protein per ml was applied to a controlled pore glass column ($0.9 \times 10$ cm) equilibrated with 0.01 M potassium phosphate, pH 7.4. The column was subsequently developed as follows: (a) 50 mls of column equilibration buffer, (b) 50 ml of 0.1 M Tris.HCl, pH 8.0, buffer and (c) 50 mls of 0.1 M Tris.HCl buffer, pH 8.0, containing 0.5 M tetramethylammonium chloride. Out of the total interferon activity 500,000 ref. units applied to the column, 450,000 ref. units appeared in fraction (c). This fraction also contained 15 mg of protein. This represents about a 90% interferon recovery and a 6 fold purification. Identical results were obtained when silicic acid was used in place of the controlled pore glass.

Interferon from the controlled pore glass column was diluted (1:1) with 0.1 M sodium acetate buffer, pH 4.5, to reduce the concentration of tetramethylammonium chloride to 0.25 M. The pH of the diluted interferon was adjusted to 4.5 and the interferon was applied to a column ($0.9 \times 10$ cm) of CM-Sepharose CL-6B equilibrated with 0.1 M sodium acetate, pH 4.5. The column was washed with 50 mls of column equilibration buffer and finally with 100 mls of a 0.1 M phosphate buffer containing 1 M sodium chloride, pH 7.4. No interferon activity was detectable in the breakthrough or wash steps. All bound interferon appeared when the column was eluted with the salt containing buffer. A total of 405,000 ref. units of interferon activity with 3.2 mgs of protein was recovered. This represents a 90% recovery of interferon and an additional 5 fold purification.

Interferon solution from the CM-Sepharose CL-6B column was applied directly to a Phenyl-Sepharose CL-4B column ($0.9 \times 5$ cm) equilibrated with 0.1 M potassium phosphate containing 1 M sodium chloride, pH 7.4. The column was washed with 50 mls of equilibration buffer and finally eluted with 50 mls of 0.1 M potassium phosphate containing 50% ethylene glycol at pH 7.4. A total of 375,000 ref. units of interferon 92% was recovered in 0.215 mg of protein. The specific activity of the final product was $1.74 \times 10^6$ ref. units/mg protein.

It should be pointed out that the process according to the instant invention is particularly suited for the efficient large scale commercial production of human leukocyte derived interferon using a tandem column arrangement wherein each adsorption column is physically connected to the next column. Since the desorption solvent in each step is compatible with the adsorption solvent utilized in the following steps, there is no need to incorporate any intervening operations between each step. Therefore, once the columns are physically linked, the process will run continuously from start to finish without interruption, until the final product, having the desired purity and concentration, is recovered. Alternatively, this process may be performed in a sequence of steps wherein optional intervening procedures may be inserted between the individual chromatographic steps as, for example, the insertion of additional concentration or dialysis operations at the end of each intermediate elution step. It is preferable, however, to carry out the present process using the continuous, in tandem arrangement.

It is to be understood that various changes and details, materials and steps, which have been herein described in order to explain the nature of this invention, may be made by those skilled in the art within the principle and scope of the invention. Accordingly, the present invention is not to be confined to the details set forth and this application is intended to cover such modifications or changes as may come within the scope of the following claims.

We claim:
1. A process for purifying human interferon derived from human leukocytes or lymphoblastoid cells to remove the inducing virus and other protein contaminants, to increase the specific activity of the final interferon produced about 1000 fold, and to obtain an overall interferon recovery of at least 70%, which process is carried out in a moderately acidic environment wherein the pH is never lower than 4.5, comprising the following steps in succession:
   a. subjecting a solution of crude interferon to chromatography on a glass sorbent material selected from the group consisting of Controlled-pore Glass (CPG) or Silicic Acids which has been first equilibrated with phosphate buffer to a pH between about 6.0–8.0;
   b. eluting the interferon bound to said glass sorbent material with a hydrophobic electrolyte solution having a pH between about 6.0–9.0 selected from the group consisting of an alkylamine or a cosolvent mixture comprising an electrolyte selected from the group consisting of sodium chloride or ammonium chloride combined with a polarity reducing agent selected from the group consisting of ethylene glycol and propylene glycol, either separately or in combination, for a time sufficient to produce an effluent containing said interferon;
   c. adjusting the pH of said effluent to between about 4.5–6.0 and thereafter subjecting said effluent to chromatography on a carboxymethyl derived cation exchange medium which has been first equilibrated with any known suitable buffer solution to a pH of about 4.5–6.0;
   d. eluting the interferon bound to said cation exchange medium with an eluant comprising a solution of salt and any known suitable buffer, said eluant having a final pH between about 4.5–9.0, for a time sufficient to produce an effluent containing said interferon;
   e. subjecting the effluent obtained in step (d) to chromatography on a phenyl-agarose hydrophobic sorbent material having a sorbent density between 30–50μ moles per ml, which has first been equilibrated with a buffering solution comprising a solution of salt and a suitable known buffer; and
   f. displacing the interferon bound to said hydrophobic sorbent material with an eluant comprising a mixture of about 50%–70% ethylene glycol and a buffer, thereby producing an interferon containing effluent having a final average specific activity between about $1 \times 10^6 - 1 \times 10^7$ ref. units/mg of protein depending upon the titer of the crude interferon starting material.

2. The process according to claim 1 wherein the human interferon starting material may be optionally subjected to a molecular filtration or membrane sieving operation, or a series of such operations prior to initiating the purification process to physically remove the inducing virus and to initially purify and concentrate the interferon preparation.

3. The process according to claim 2 wherein the concentrated human interferon recovered in step (e) is further subjected to molecular sieving prior to initiating step (f).

4. The process according to claim 3 wherein the purified interferon obtained in step (f) may be further filtered, sterilized and lyophilized rendering said interferon safe for clinical use in humans.

5. The process according to claim 4 where the chromatographic materials described in steps (a), (c) and (e) are arranged in tandem so that the purification process proceeds as a continuous operation to minimize the time required for purification and to reduce final product loss.

6. The process according to claim 5 wherein the purified interferon obtained in step (f) may be optionally dialyzed to remove the ethylene glycol.

7. The process according to claim 6 wherein, when said phenyl-agarose has a ligand density lower than 40μ moles per ml of sorbent, the purification process may be modified such that the interferon bound to said phenylagarose in step (e) may be displaced from said phenylagarose with buffer alone, thereby eliminating the ethylene glycol utilized in step (f).

8. The process according to claim 7 wherein the final interferon produced in step (f) of said purification process is the natural form of said interferon which comprises those components normally present in unpurified human leukocyte interferon which are labile in an acidic environment along with those components which are stable in an acidic environment.

9. The process according to claim 8 wherein said hydrophobic electrolyte solution in step (b) is an alkylamine selected from the group consisting of methylamine, dimethylamine, trimethylamine and tetramethylamine.

10. The process according to claim 8 wherein said hydrophobic electrolyte solution in step (b) is a cosolvent mixture buffered to a pH between about 6.0–9.0 with Tris.HCl or phosphate buffer having a pH between about 6.0–9.0.

11. The process according to claim 1 wherein the interferon starting material is obtained from cultured established human lymphoblasts selected from the group consisting of Namalva and DG-75.

12. The process according to claim 1 wherein the human blood leukocyte cells used in producing said crude interferon are obtained from buffy coat cells and are separated from the residual erythrocytes present in the buffy coat cells by:
   a. contacting said buffy coat cells with a suitable starch gel agglomerating solution thereby causing the majority of erythrocytes to agglomerate and settle out of the mixture by gravity sedimentation;
   b. collecting the top layer of the sediment containing the leukocyte cells;
   c. washing said leukocyte cells with physiological saline; and
   d. thereafter resuspending said leukocyte cells in a suitable interferon production medium.

13. The process according to claim 12 wherein the starch gel used in making said starch gel agglomerating solution is hydroxyethyl starch (HES).

14. The process according to claim 13 wherein a protein supplement is added to said production medium which supplement is selected from the group consisting of human serum, human a-gamma and human a-gamma plasma at a concentration between about 2%–10% v/v of said production medium, which supplement is first subjected to chromatography on a glass adsorbent material selected from the group consisting of Controlled-pore Glass (CPG) and Silicic Acids, and further subjected to chromatography on phenyl-agarose hydrophobic sorbent material to remove those protein components normally found in said protein supplement which would contaminate and copurify with the final interferon isolated during said purification process.

15. The process according to claim 14 wherein an interferon inducing virus is added to said production medium after first subjecting the virus preparation to chromatography on phenyl-agarose hydrophobic sorbent material to remove those protein components normally found in said production medium which would contaminate and copurify with the final interferon isolated during said purification process.

* * * * *

UNITED STATES PATENT AND TRADEMARK OFFICE
CERTIFICATE OF CORRECTION

PATENT NO. : 4,485,038　　　　　　　　　　　　　　　Page 1 of 2
DATED : November 27, 1984
INVENTOR(S) : Kailash C. Chadha and Eugene Sulkowski It is certified that error appears in the above-identified patent and that said Letters Patent are hereby corrected as shown below:

Title Page, line 12, (second col. appearing on that page), change "Chada" to --Chadha--

Title Page, line 16, (second col. appearing on that page), change "Chada" to --Chadha--

In the Abstract, line 2, change "of" to --or--

Col. 1, line 40, change "know" to --known--

Col. 1, line 62, change "ph" to --pH--

Col. 2, line 30, change ""ph2-labile"" to --"pH2-labile"--

Col. 3, line 33, change "combination" to --combination:--

Col. 3, line 54, change "seiving" to --sieving--

Col. 3, line 55, change "seiving" to --sieving--

Col. 4, line 27, change ""physiologicalsaline"" to --physiological saline--

UNITED STATES PATENT AND TRADEMARK OFFICE
CERTIFICATE OF CORRECTION

PATENT NO. : 4,485,038

DATED : November 27, 1984

INVENTOR(S) : Kailash C. Chadha and Eugene Sulkowski

It is certified that error appears in the above-identified patent and that said Letters Patent are hereby corrected as shown below:

Col. 4, line 37, change "Necastle" to --New Castle--

Col. 5, line 26, change "physiologica" to --physiological--

Col. 10, line 14, change "Hauupange" to --Hauppange--

Col. 10, line 22, change "Tri" to --Tris--

Col. 11, line 46, change "recoverd" to --recovered--

Col. 11, line 58, change "recoverd" to --recovered--

Claim 1, line 13, change "Acids" to --Acid--

Claim 14, line 4, change "a-gamma and" to --a-gamma serum and--

Claim 14, line 9, change "Acids," to --Acid,--

Signed and Sealed this

Eighteenth Day of June 1985

[SEAL]

Attest:

DONALD J. QUIGG

Attesting Officer    Acting Commissioner of Patents and Trademarks